United States Patent
Verkade (10) Patent No.: US 7,261,700 B2
(45) Date of Patent: Aug. 28, 2007

(54) ROTATABLE STRAP TAB CAP

(75) Inventor: Drew Verkade, Carlsbad, CA (US)

(73) Assignee: DJO, LLC, Vista, CA (US)

( * ) Notice: Subject to any disclaimer, the term of this patent is extended or adjusted under 35 U.S.C. 154(b) by 0 days.

(21) Appl. No.: 11/094,724

(22) Filed: Mar. 30, 2005

(65) Prior Publication Data

US 2005/0222530 A1 Oct. 6, 2005

Related U.S. Application Data (60) Provisional application No. 60/558,402, filed on Mar. 31, 2004.

(51) Int. Cl.
*A61F 5/00* (2006.01)
(52) U.S. Cl. .............. 602/23; 602/5; 602/20
(58) Field of Classification Search .......... 602/16, 602/5, 6, 12, 19–23, 26–29; 24/324, 662, 24/3.1, 115 K, 265 AL, 265 A, 265 BC; 403/374.1, 374.2, 373; 128/201.11, 201.29, 128/207.11
See application file for complete search history.

(56) References Cited

U.S. PATENT DOCUMENTS

| | | | |
|---|---|---|---|
| 49,305 A | 8/1865 | Ruggles | |
| 243,605 A | 6/1881 | Ott | |
| 932,177 A | 8/1909 | Roth | |
| 1,927,061 A | 9/1933 | Chapman | |
| 2,090,367 A | 8/1937 | Janes | |
| 2,615,218 A | 10/1952 | Ross | |
| 2,636,234 A | 4/1953 | Reiter | |
| 2,928,153 A * | 3/1960 | Reiter | ............... 24/703.4 |
| 3,528,412 A | 9/1970 | McDavid | |
| 4,291,822 A | 9/1981 | Simonds | |
| 4,773,404 A | 9/1988 | Townsend | |
| 4,955,369 A | 9/1990 | Bledsoe et al. | |
| 5,086,760 A | 2/1992 | Neumann et al. | |
| 5,288,287 A | 2/1994 | Castillo et al. | |
| 5,292,303 A | 3/1994 | Bastyr et al. | |
| 5,383,845 A | 1/1995 | Nebolon | |
| 5,409,449 A | 4/1995 | Nebolon | |
| 5,458,565 A | 10/1995 | Tillinghast, III et al. | |
| 5,624,390 A | 4/1997 | Van Dyne | |
| 6,425,166 B1 | 7/2002 | Seligman et al. | |
| 6,845,548 B1 * | 1/2005 | Lin | ............... 24/265 BC |
| 2005/0148917 A1 * | 7/2005 | Nathanson | ............... 602/23 |

* cited by examiner

*Primary Examiner*—Justine R. Yu
*Assistant Examiner*—Shumaya B. Ali
(74) *Attorney, Agent, or Firm*—Knobbe, Martens, Olson & Bear LLP (57) ABSTRACT

The present application describes a strap tab cap assembly for connecting a strap tab to an article, such as a knee brace frame. The assembly includes a strap tab cap disposed over a washer having two upwardly extending flanges. A bushing and fastening member are provided for rotatably coupling the strap tab cap to the knee brace frame. However, the washer is rotatably fixed with respect to the knee brace frame. The flanges on the washer limit the rotation of the strap tab cap with respect to the knee brace frame. The washer also protects the knee brace frame from wear during rotation of the strap tab. The assembly is very durable and is resistant to becoming disassembled during normal use, but includes field replaceable components for easy repair.

28 Claims, 7 Drawing Sheets

FIG. 7

ROTATABLE STRAP TAB CAP

RELATED APPLICATIONS

The present application claims priority under 35 U.S.C. §119(e) to U.S. provisional application Ser. No. 60/558,402, filed on Mar. 31, 2004, which is hereby expressly incorporated by reference in its entirety.

BACKGROUND OF THE INVENTION

1. Field of the Invention

The present invention relates to connection devices for connecting straps to various articles, such as knee brace frames.

2. Description of the Related Art

The human knee generally comprises an articulating joint between the thigh and calf muscle groups that supports the weight of the body while a person is standing, walking or running. The joint is primarily held together by four ligaments, namely, the anterior and posterior cruciate ligaments and the medial and lateral collateral ligaments. The knee is a relatively weak joint and therefore knee injuries arising out of cartilage damage, ligament strain, and other causes are relatively commonplace. Knee injuries are particularly likely to occur during physical activities in which the knees are subjected to significant lateral loads. Among the numerous physical activities in which knee injuries occur, skiing and motorcycle racing have proven to be particularly hazardous.

Figure 1:
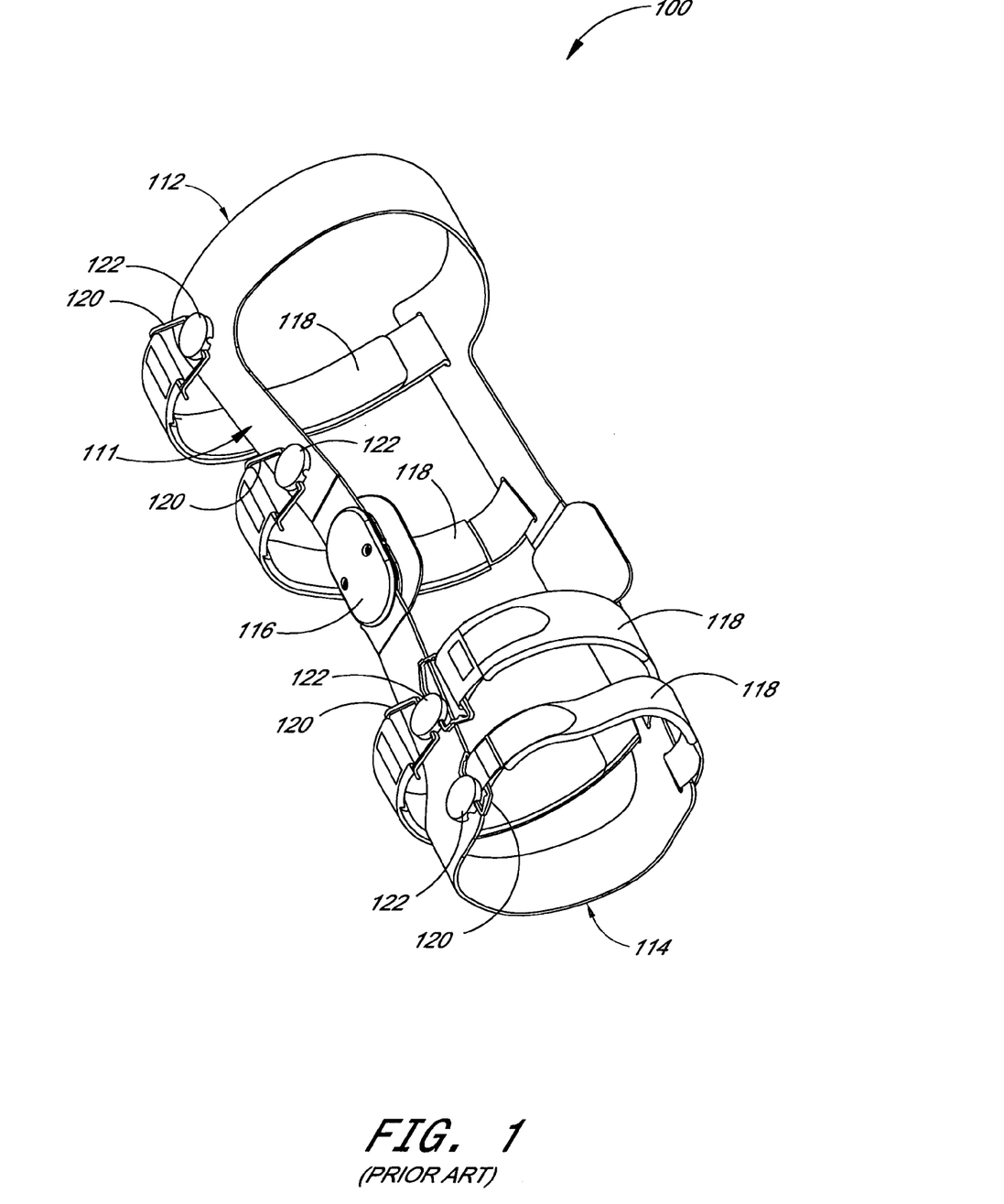
FIG. 1 is a perspective view of a knee brace of the type known in the art.

To help prevent knee injuries, various types of "preventive" knee braces have been proposed to help support and reinforce the knee. For example, a knee brace 100 of the type known in the art is shown in FIG. 1. The illustrated knee brace 100 includes a rigid frame 111 having an upper member 112 and a lower member 114. Polycentric hinges 116 connect the upper and lower members together along the knee joint. The rigid frame 111 maintains the thigh and calf in the proper alignment and thereby prevents lateral knee joint displacement and hyperextension of the lower leg. A plurality of straps 118 is used to secure the upper member 112 and lower member 114 of the frame 111 to the respective thigh and calf portions of the leg. During fitting, each strap 118 is passed through a loop-shaped connector called a strap tab 120 and is then folded over onto itself for securement with Velcro®. Each of the strap tabs 120 is coupled to the frame 111 by a rigid connection device, called a strap tab cap 122.

In practice, it has been found that strap tab caps, such as those illustrated on the knee brace of FIG. 1, suffer from a variety of shortcomings that limit their effectiveness as a connection device. For example, the strap tab cap is typically constructed as a relatively thick member for receiving attachment screws. As a result, the strap tab cap may have a relatively high profile that protrudes outward from the surface of the frame. The high profile of the strap tab cap is undesirable because it increases the possibility that the strap tab cap will catch or snag on a foreign object during physical activity.

Another significant shortcoming relates to the manner in which the strap tab cap is mounted to the knee brace frame. Typically, the strap tab cap is rigidly connected to the knee brace frame. As a result, the strap tab cap cannot rotate relative to the knee brace frame to allow for adjustment of the strap position. This is disadvantageous because it is desirable for the straps on a knee brace to be adjustable for conforming to the shape of the user's leg. In recent years, certain rotatable strap tab cap mechanisms have been proposed for use with knee brace frames in an attempt to overcome this and other shortcomings. However, under certain conditions, existing rotatable strap tab caps may lack the structural integrity necessary for effective use as a connection device.

Thus, a very real and substantial need exists for a rotatable strap tab cap that overcomes the shortcomings of the existing schemes. It is desirable that such a strap tab cap has a low profile to avoid interfering with foreign objects during physical activity. It is also desirable that such a strap tab cap allows the position of the strap to be adjusted according to the user's needs. It is also desirable that such a strap tab cap is constructed of a durable material that is resistant to corrosion. Finally, to be practical, it is desirable that such a strap tab cap is inexpensive to manufacture and is aesthetically appealing. The present invention addresses this need.

SUMMARY OF THE INVENTION

Embodiments of the present rotatable strap tab cap have several features, no single one of which is solely responsible for their desirable attributes. Without limiting the scope of this rotatable strap tab cap as expressed by the claims that follow, its more prominent features will now be discussed briefly. After considering this discussion, and particularly after reading the section entitled "Detailed Description of the Preferred Embodiments," one will understand how the features of the preferred embodiments provide a variety of advantages. For example, the strap tab cap may allow pivoting of the strap tab relative to a rigid frame member, thus providing better fit and comfort. The strap tab cap may also provide the ability to track wearer motion and the ability to accommodate dimensional variations in frames. Furthermore, the strap tab cap provides a field replaceable fastening member that does not back out after repeated rotations and is not visible when the brace is worn. Still further, the strap tab cap has an aesthetically pleasing construction and may be manufactured inexpensively.

One embodiment of the present rotatable strap tab cap secures a strap tab to a rigid frame member of an orthopedic brace. The strap tab cap comprises a cap, a strap tab, a washer, a bushing, and a fastening member. The fastening member extends from an inside surface of the frame member, through the bushing, through an aperture in the frame member, through the washer and into the cap, and the strap tab extends through a channel in an underside of the cap.

In another embodiment, a strap tab cap assembly is provided for attaching a strap tab to a knee brace frame. The strap tab cap assembly includes a strap tab cap having a main body and a cap shaft extending from the bottom side. The cap shaft is formed to extend into a hole in the knee brace frame. A channel extends along the bottom side of the main body for receiving a first portion of the strap tab for securely attaching the strap tab to the knee brace frame. A bushing is disposed along an inner surface of the knee brace and includes a shaft portion formed to extend into the hole. The bushing shaft is sized for slidable engagement with the cap shaft. The bushing shaft and the cap shaft preferably have complementary cross-sections for maintaining the bushing and the strap tab cap in a rotatably fixed relationship. In one advantageous feature, a distance between the bushing and strap tab cap may be adjustable for conforming to the thickness of the knee brace frame.

In another embodiment, a strap tab retainer is provided for connection to an article, wherein the article includes a wall formed with a hole extending therethrough. The strap tab retainer includes a first strap tab for connecting a strap to the knee brace frame. A washer is provided having a central hole intended for alignment with a hole in the article wall. The washer has a structure matable with the article wall to prevent rotation of the washer. A clamp engages the interior surface of the wall of the article and the exterior surface of the washer. The clamp is rotatable about the hole and holds the first strap tab against the top surface of the washer. The washer is formed with stops for engaging a portion of the clamp whereby limited rotation of the strap tab is permitted by rotation of the clamp while the washer remains substantially stationary with respect to the article.

In one method, a knee brace having an outer surface is provided. A washer is disposed along the outer surface of the knee brace frame, wherein the washer has a bottom side configured for engagement with the knee brace frame. The method further comprises placing a portion of a strap tab along an outer surface of the washer, wherein the strap tab is configured for holding a securing strap for assisting in securing the knee brace to a user's leg. During use, the strap tab is rotated with respect to the outer surface of the washer while maintaining the washer substantially stationary with respect to the knee brace.

In another embodiment, a strap tab retainer is provided for connection to an article, wherein the article includes a wall formed with a hole extending therethrough. A washer having a central hole is provided for alignment with the hole in the article wall and the washer includes a means for engaging the article wall to prevent rotation of the washer. A strap tab holder is disposed along the top surface of the washer. The strap tab holder includes a ring retaining structure for holding a portion of a strap tab against the top surface of the washer. The washer is formed with a means for engaging a portion of the strap tab holder whereby limited rotation of the strap tab is permitted by rotation of the strap tab holder while the washer remains substantially stationary with respect to the article.

In another embodiment, a connection device for connecting a strap to a knee brace is provided. The knee brace has an elongate side support formed with a hole at a location desirable for the strap. The connection device comprises a spool-shaped member having first and second end portions, each having cross-sections greater than the hole. The first and second end portions are connected by a central generally cylindrical shaft. The cylindrical shaft is adjustable in length and sized to fit for rotational movement in the hole. The connection device further comprises a D-ring sized to hold a strap. The first end portion includes a channel extending through and spaced from the cylindrical shaft. The channel extends along an underside of the first end portion to hold the D-ring, such that any force applied to the D-ring by a strap connected thereto passes through the central cylindrical shaft.

BRIEF DESCRIPTION OF THE DRAWINGS

Embodiments of the present rotatable strap tab cap will now be discussed in detail. The embodiments depict a novel and non-obvious rotatable strap tab cap as illustrated in the accompanying drawings labeled FIGS. 2 through 7, which are for illustrative purposes only.

DETAILED DESCRIPTION OF THE PREFERRED EMBODIMENTS

Various embodiments of the present invention depict an improved strap tab cap assembly configured for connecting a loop-shaped strap tab to a knee brace frame. The primary components of the strap tab cap assembly may rotate as a single unit, thereby reducing mechanical wear during use. The assembly also protects the knee brace frame from wear and provides excellent pull strength such that the strap tab cannot be inadvertently detached from the knee brace during normal use. Still further, the assembly provides positive and reliable mechanical stops for limiting the rotation of the strap tab with respect to the knee brace frame. In another advantageous feature, the strap tab cap assembly is adaptable for use with a wide variety of knee brace frames and has a low profile construction.

Although embodiments of the assembly are configured for use with a knee brace, it should be appreciated that the principles and aspects of the embodiments disclosed and discussed herein are also applicable to a variety of other devices having different structures and functions. For example, alternative assembly embodiments may be configured for use with items such as luggage, backpacks, or in any other application wherein it is desirable to attach a strap to an article. The manner of adapting the embodiments described herein to various other devices and functionalities will become apparent to those of skill in the art in view of the description that follows.

Figure 2:
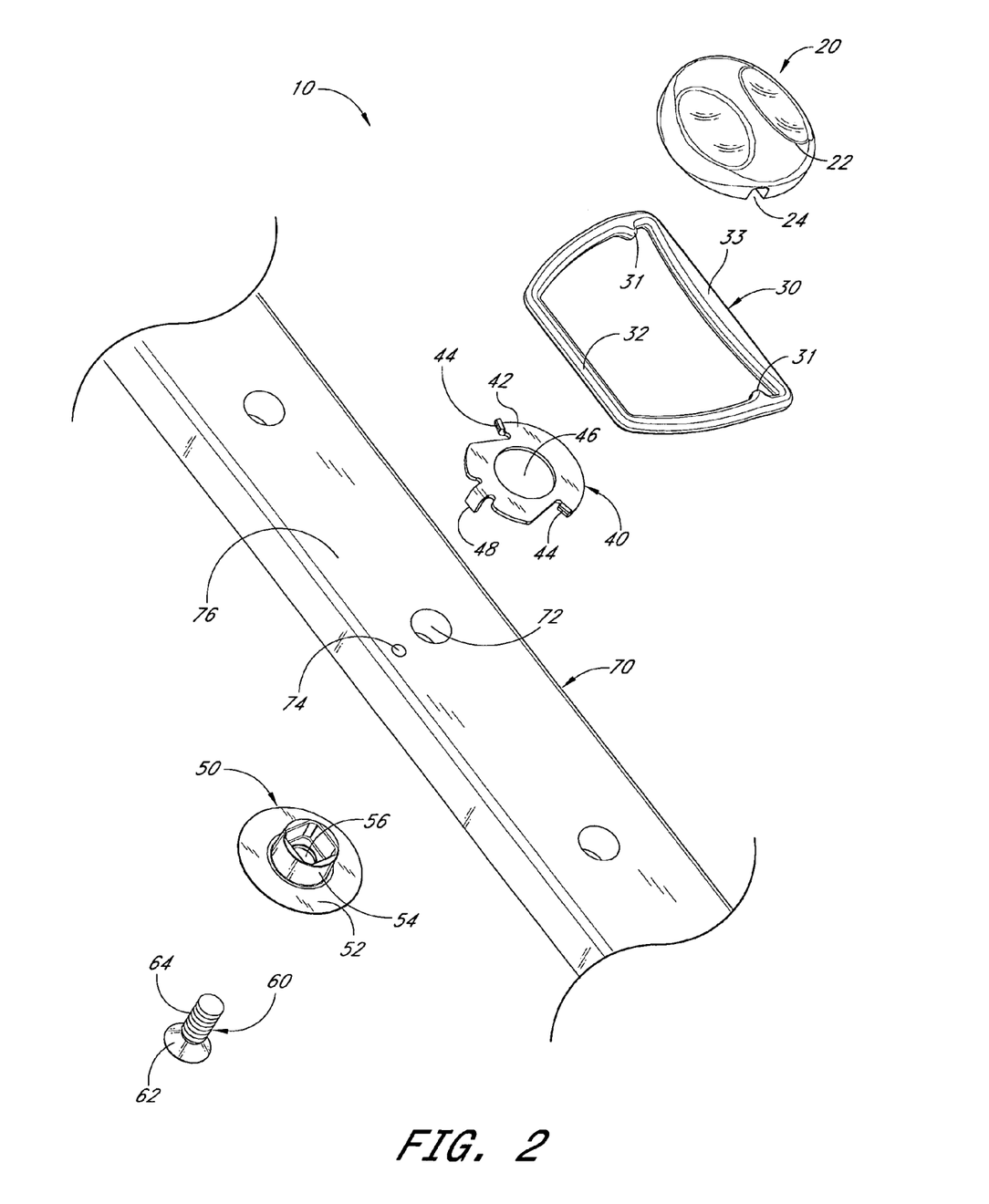
FIG. 2 is an exploded view of one embodiment of an improved rotatable strap tab cap assembly according to the present invention.

With reference now to FIG. 2, an exploded view of one embodiment of an improved rotatable strap tab cap assembly 10 is shown. The rotatable strap tab cap assembly 10 comprises a strap tab cap 20, a retaining washer 40, a bushing 50 and a fastening member 60. In the illustrated embodiment, the strap tab cap assembly 10 provides an improved strap tab retaining mechanism for rotatably coupling a strap tab 30 to a knee brace frame 70. Although the strap tab 30 is shown as a loop-shaped member for purposes of illustration, those of skill in the art will appreciate that the strap tab may take a variety of different forms. For example, the strap tab may be a rod or a curved member and need not take the form of a loop-shaped member. However, in some embodiments, the strap tab is a loop-shaped member, sometimes referred to as a D-ring, which is formed of a metallic material, such as steel.

In the illustrated embodiments, the strap tab 30 includes protrusions 31 on opposing sides that help to retain a strap in position on a first side 33 of the strap tab 30. Those of ordinary skill in the art will appreciate that the protrusions 31 need not be provided. Further, in the illustrated embodiments portions of the strap tab 30 have substantially rectangular cross-sections. However, those of ordinary skill in the art will appreciate that these cross-sectional shapes could be different. For example, they could be cylindrical.

The strap tab cap 20 generally comprises a substantially flat main body 22 having a channel 24 extending laterally along a bottom side. The channel 24 is sized for receiving a portion 32 of the strap tab 30 such that the strap tab cap 20 provides a rugged and reliable strap tab holding mechanism. The strap tab cap is preferably made of a polymeric material, such as nylon, or a metallic material. The retaining washer 40 is preferably positioned between the strap tab cap 20 and an outer surface 76 of the knee brace frame 70. The retaining washer preferably comprises a thin body 42 formed with a central hole 46 configured for alignment with a first hole 72 in the frame 70. The washer 40 is also provided with a downwardly extending tab 48 for insertion into a second hole 74 in the frame 70. When assembled, the tab 48 prevents the retaining washer 40 from rotating relative to the frame 70. The retaining washer 40 is further provided with first and second stops, preferably in the form of first and second flanges 44, for limiting the rotation of the strap tab cap assembly 10 with respect to the frame 70. In some embodiments, the washer is formed of a metallic material, such as stainless steel.

The bushing 50 comprises a body 52 and a shaft 54 configured for slidable engagement with the strap tab cap 20, as will be described in more detail below. When assembled, the body 52 of the bushing 50 is located along an inner surface of the frame 70. The body is sized to engage the inner surface of the frame while the shaft extends at least partially through the hole in the frame. The bushing is preferably made of a polymeric or metallic material. As will be described in more detail below, in certain embodiments, it is desirable for the bushing 50 to be formed of a flexible material, such as nylon, for allowing the body 52 to conform to a frame having a curved inner surface.

The fastening member preferably includes a head portion 62 and a threaded body 64. The threaded body 64 extends through a central hole 56 in the bushing 50 for engagement with the strap tab cap 20, thereby rotatably coupling the strap tab cap assembly 10 to the knee brace frame 70. In this configuration, the fastening member including its head portion 62 and the cap 20, can form a clamp. Additionally, the fastening member, including its head portion 62 and the cap 20, can form a spool-shaped member. The fastening member is preferably made of a metallic material, such as steel with plating.

Figure 3:
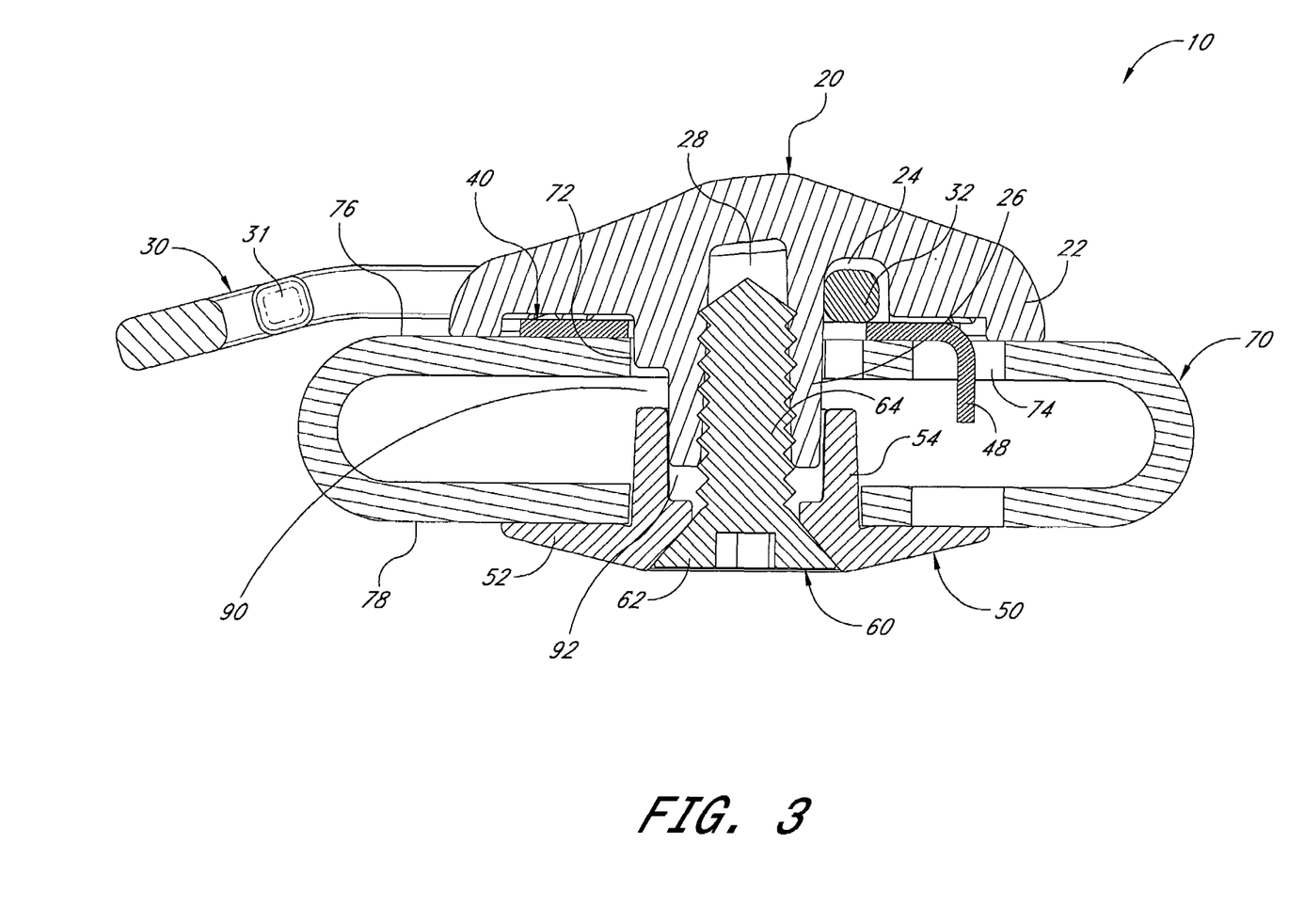
FIG. 3 is a cross-sectional view of the strap tab cap assembly of FIG. 2 in an assembled state.

With reference now to FIG. 3, a cross-sectional view of the strap cap assembly 10 is shown. In this view, it can be seen that the strap tab cap 20 includes a cap shaft 26 that extends into the knee brace frame 70. More particularly, the cap shaft 26 is configured to extend through the hole in the retaining washer 40 and also through the first hole 72 in the knee brace frame 70. The tab 48 on the washer is held within the second hole 74 in the frame 70. As illustrated, the shaft 54 on the bushing 50 also extends into the frame 70 and is preferably configured to slidably engage the cap shaft 26. Upper and lower clearances 90, 92 are preferably provided between the strap tab cap 20 and the bushing 50. The clearances 90, 92 provide design flexibility such that the strap tab cap assembly 10 is capable of being mounted on a variety of different knee brace frames having different dimensions. In some embodiments, the cap shaft 26 fits inside the bushing shaft 54. However, in alternative embodiments, the bushing shaft 54 may fit inside the cap shaft 26 or the two shafts may be configured such that they abut one another or do not contact each other at all. Although not required, the cap shaft 26 and the bushing shaft 54 are preferably formed with complementary cross-sectional shapes. Accordingly, when the shafts 26, 54 slidably engage one another, the cap 20 and the bushing 50 rotate as a unit. Examples of cross-sectional shapes include, for example, square cross-sections and hexagonal cross-sections.

The fastening member 60 preferably extends from the inside surface 78 of the frame 70, through the bushing 50 and into a central orifice 28 in the shaft 26 of the strap tab cap 20. As illustrated, the threaded body 64 of the fastening member 60 engages an inner wall along the orifice 28 of the strap tab cap 20 for securely coupling the strap tab cap 20 to the bushing 50. In some embodiments, the inner wall of the orifice 28 is manufactured from a material that is soft enough to receive the threads as the fastening member 60 is screwed into the orifice 28. However, in alternative embodiments, a variety of other fastening members and cap materials may be used to securely attach the bushing 50 and strap tab cap 20 together.

During use, the cap 20, bushing 50, fastening member 60 and strap tab 30 preferably rotate as a single unit while the retaining washer 40 remains substantially fixed with respect to the frame 70. Accordingly, the strap tab cap 20, the bushing 50, and the fastening member 60 cooperate to provide one embodiment of a rotatable clamp or clasp that holds a portion of the strap tab against the washer while allowing for rotation of the strap tab relative to the frame 70. In the assembled condition, the cap 20 and bushing 50 combine to provide a spool-shaped member that is rotatable within the first hole 72. The cap provides a first end portion and the bushing provides a second end portion of the spool shaped member. The first and second end portions are sized with cross-section larger than the hole for maintaining the spool shaped member in the first hole. The fastening member 60 retains the spool-shaped member in the illustrated configuration.

As the strap tab 30 rotates relative to the frame 70, the attachment portion 32 of the strap tab 30 slides along the surface of the washer 40, rather than along the outer surface 76 of the frame 70. Accordingly, the washer 40 protects the frame 70 from wear during rotation of the strap tab 30. This is an advantageous feature because the washer 40 is preferably constructed of a durable metal, whereas the frame 70 is typically formed from a softer material, such as, for example, a carbon fiber or plastic. However, the strap tab cap assembly may be used with any type of frame including metal frames made of aluminum, steel or titanium.

When assembled, the attachment portion 32 of the strap tab 30 is securely held within the channel 24 extending laterally through the strap tab cap body 22 for coupling the strap tab 30 to the knee brace frame 70. The channel 24 is preferably formed with a sufficient size such that the attachment portion 32 may pivot within the channel for allowing the strap tab 30 to pivot outward relative to the frame 70. This pivoting motion enables the user to more easily pass a flexible strap through the loop of the strap tab 30, and the additional degree of freedom also substantially increases the fit and comfort of the knee brace during use.

With continued reference to the particular view illustrated in FIG. 3, during use, tension in the strap will typically pull the strap tab 30 to the left. However, because the attachment portion 32 of the strap tab 30 passes through the channel 24 on the right side of the strap tab cap 20, the forces are transferred through the shaft 26 of the strap tab cap 20 and through the fastening member 60. Accordingly, the arrangement of components substantially increases the shear strength (i.e., pull strength) of the strap tab cap assembly 10 as compared to a configuration wherein the strap tab 30 is coupled to the strap tab cap 20 on the opposite side. Furthermore, the bushing body 52 and fastening member head 62 are configured to maintain the assembly in a rigid configuration for preventing the strap tab cap 20 from lifting off the surface of the knee brace frame 70. Accordingly, some embodiments of the strap tab cap assembly 10 described herein provide excellent structural integrity and minimize the risk of a mechanical failure during use. Although the strap tab cap assembly is preferably used in the manner described above, if desired, the strap tab may also be flipped or reversed such that the force is directed away from the fastening member, rather than through the fastening member. In such case, it may be advantageous to make the cap of steel or other strong metal. Still further, the strap tab cap may be formed with two channels for coupling two strap tabs to the knee brace frame. In this embodiment, the strap tabs may each extend away from the fastener. Alternatively, the strap tabs may be configured to overlap (with appropriate shapes to avoid interference with one another) such that the force from each of the strap tabs is directed toward the fastener.

In another advantageous feature, the bushing 50 is preferably formed with a low profile for minimizing the protrusion of the bushing from the inside surface 78 of the frame 70. The low profile advantageously reduces interference between the bushing 50 and the user's leg. In one embodiment, the bushing 50 extends about 0.08" or less beyond the inside surface of the frame. In some embodiments, the fastening member 60 is located within the bushing 50, such that the fastening member 60 also does not interfere with the user's leg.

Figure 4:
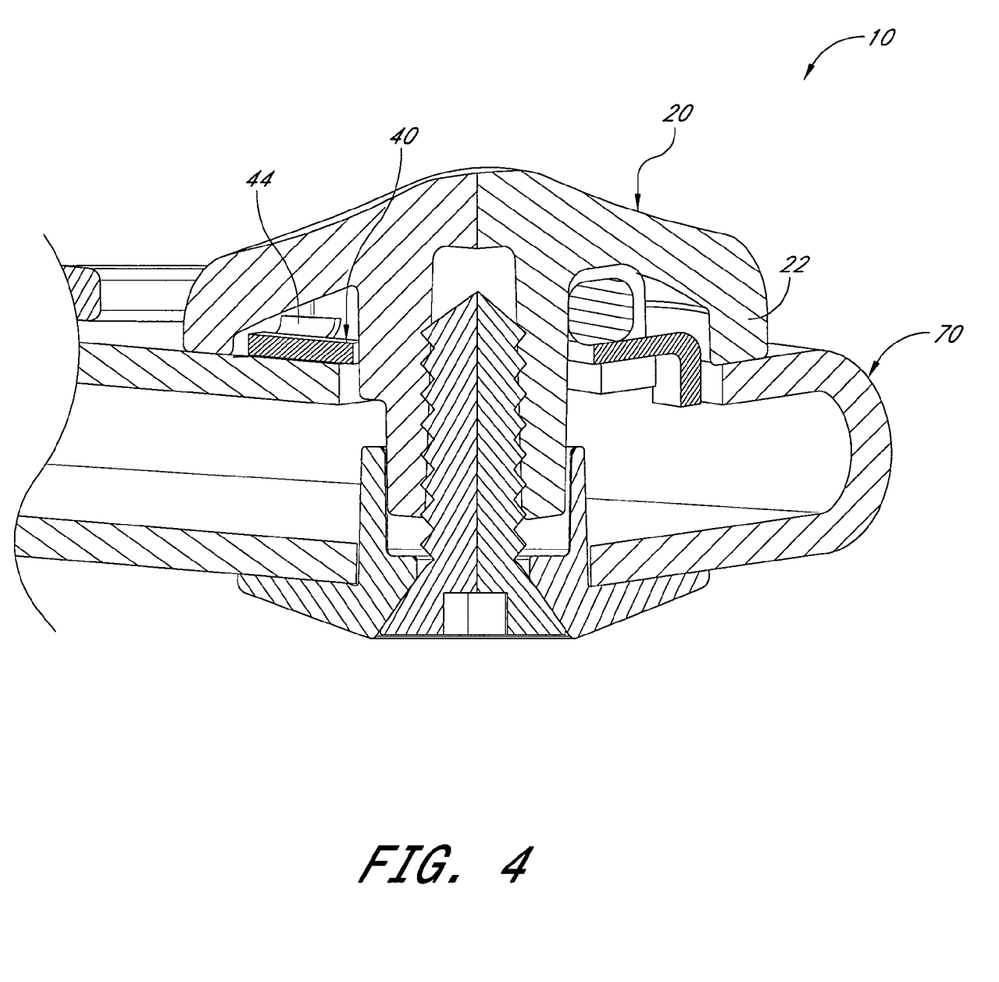
FIG. 4 is another cross-sectional view of the strap tab cap assembly wherein the assembly has been cut-away along two directions to illustrate the interaction of the components.

With reference now to FIG. 4, an additional portion of the strap tab cap assembly 10 has been cut-away to expose the location of one of the flanges 44 on the retaining washer 40 with respect to the body 22 of the strap tab cap 20. As described above, in the assembled condition, the washer 40 is fixed with respect to the frame 70 while the remaining components of the strap tab cap assembly 10 are rotatable with respect to the frame. The illustrated flange 44 is located within the strap tab cap 20 at a location wherein the flange will contact a portion of the strap tab cap after a fixed amount of rotation. In this manner, the interaction between the flanges 44 and the strap tab cap 20 defines the rotational limits of the strap tab cap assembly 10 with respect to the knee brace frame 70. Some embodiments of the present invention include a washer having flanges, however, those skilled in the art will appreciate that a wide variety of alternative stops may be used to provide the strap tab cap assembly with rotational limits without departing from the scope of the invention.

Figure 5A:
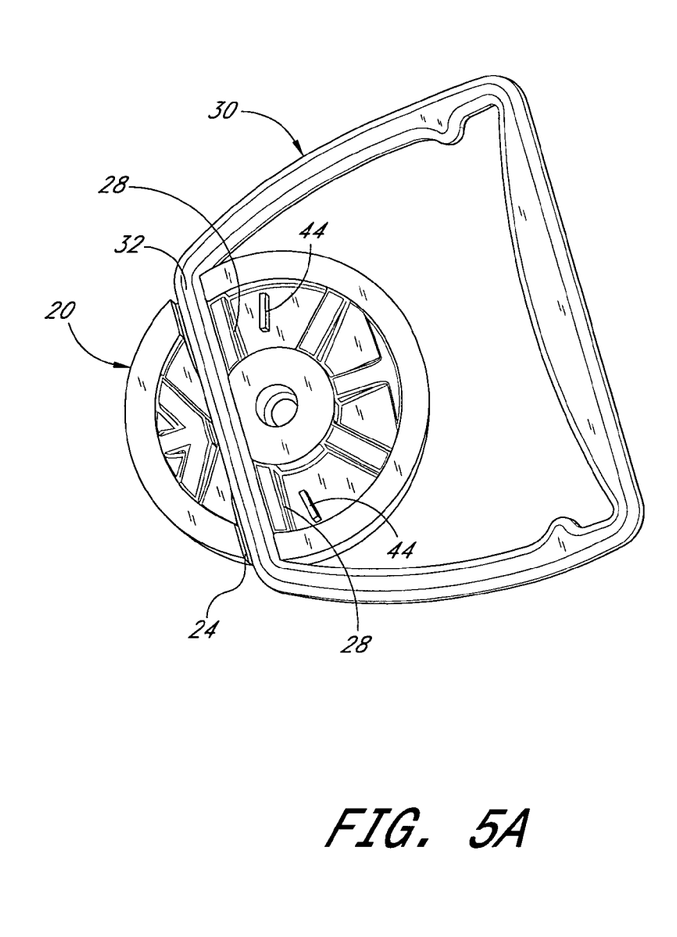
FIG. 5A is a bottom cross-sectional view illustrating the strap tab cap in a neutral position.
Figure 5B:
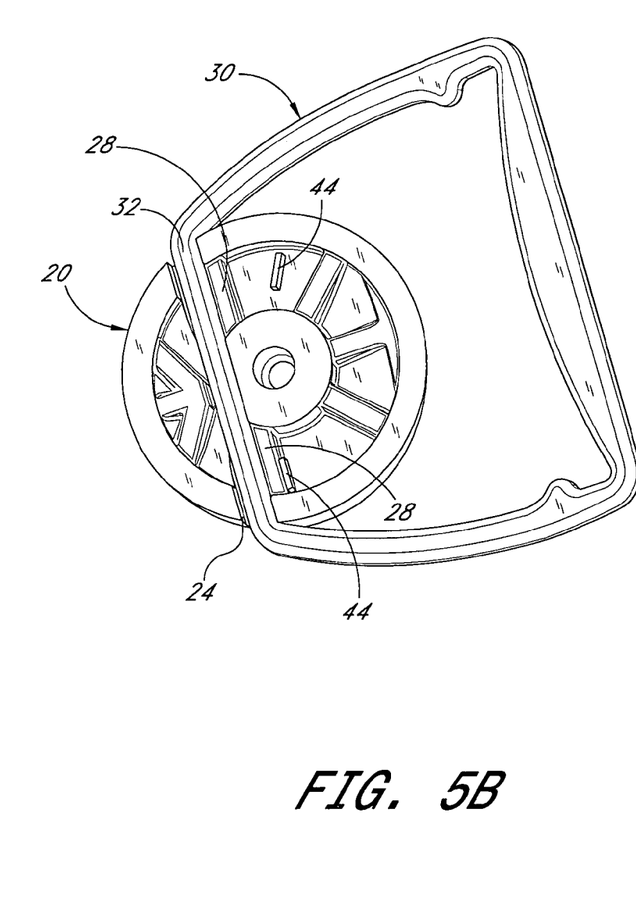
FIG. 5B is another bottom cross-sectional view wherein the strap tab cap is abutting a stopping mechanism for preventing further rotation.

With reference now to FIGS. 5A and 5B, cut-away bottom views of the strap tab cap 20 are provided for ease of understanding. In this view, the upper portions of the washer flanges 44 are illustrated in isolation (i.e., without the rest of the washer). As discussed above, the channel 24 extends laterally through the cap 20 for receiving a portion 32 of the strap tab 30. The channel 24 is defined in part by an interior wall 28, which is also configured for contacting the flanges 44. More particularly, when the wall 28 contacts the flanges 44, the strap tab cap 20, and therefore the entire strap tab cap assembly, is prevented from further rotation. Therefore, as discussed above, the contact between the cap 20 and the washer flanges 44 defines the rotational limits of the cap 20 and the strap tab 30 with respect to the knee brace frame. Some embodiments include a strap tab cap 20 having a wall 28 configured for abutting against the flanges 44. However, those skilled in the art will appreciate that alternative strap tab cap configurations may also be used wherein a portion of the strap tab cap is adapted for contacting one or more fixed stops.

Figure 6A:
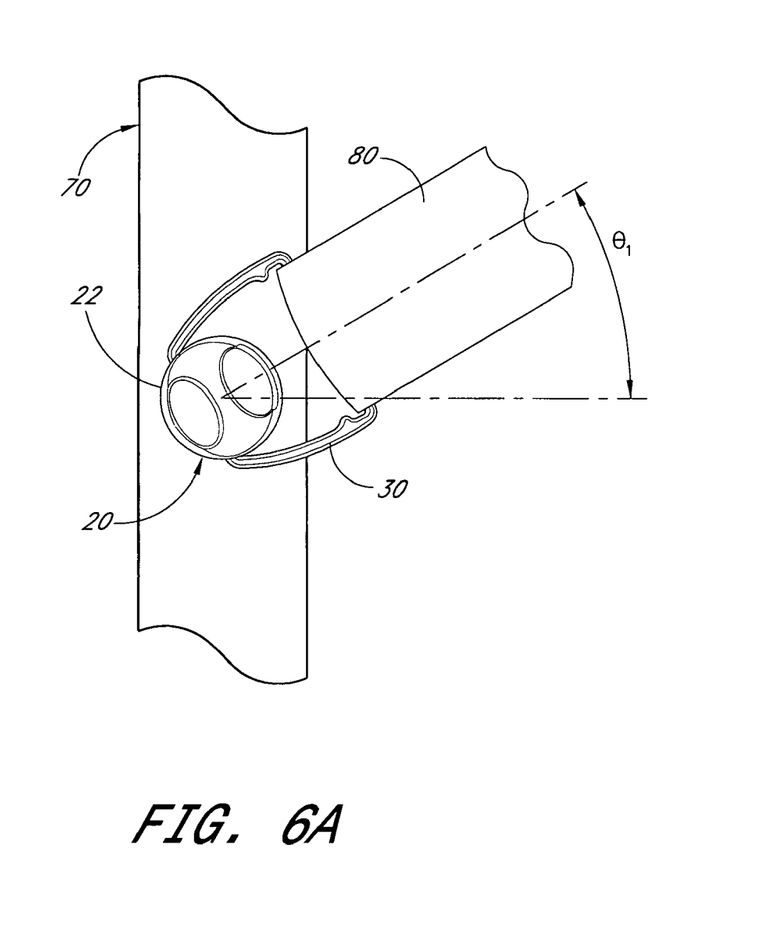
FIG. 6A is a side view illustrating an upper rotational limit of the strap tab cap of FIG. 2.
Figure 6B:
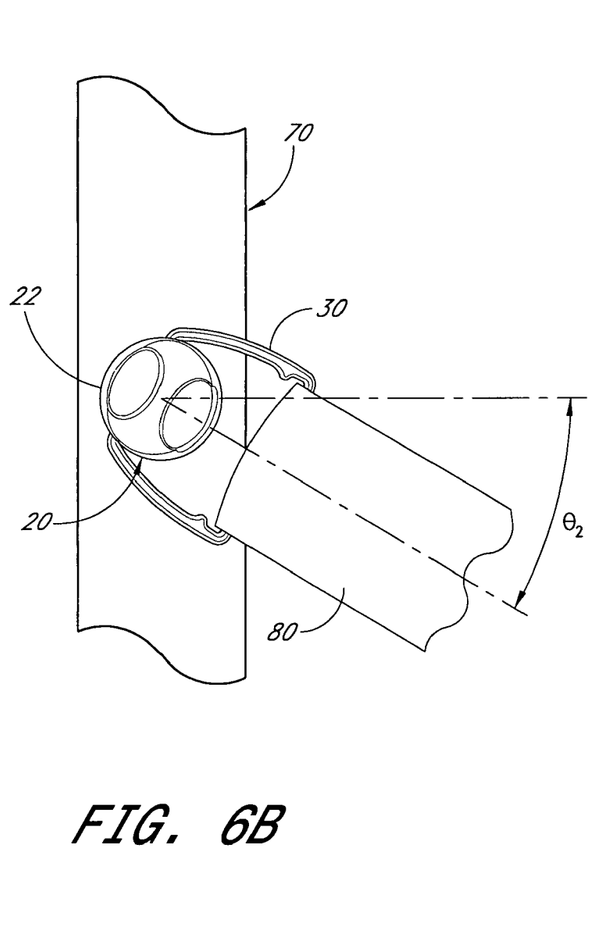
FIG. 6B is a side view illustrating a lower rotational limit of the strap tab cap of FIG. 2.

With reference now to FIGS. 6A and 6B, a side view of the strap tab cap assembly is provided for illustrating exemplifying rotational limits of the assembly. As illustrated, a strap 80 is coupled to a strap tab 30, which is rotatably coupled to the knee brace frame 70 by the strap tab cap 20. As shown in FIG. 6A, the strap tab cap 20 may be configured to rotate in a first direction relative to the knee brace frame 70 at an angle $\theta_1$. As shown in FIG. 6B, the strap tab cap 20 may also be configured to rotate in a second direction at an angle $\theta_2$. The maximum angles of rotation are preferably determined by the locations of the stops (e.g., flanges) along the washer. The range of rotational movement is preferably selected for allowing the strap 80 to be adjusted according to the shape of the user's leg. The rotation improves the comfort and effectiveness of the knee brace without sacrificing stability or support of the knee joint. The rotation also improves the comfort of the knee brace by allowing the strap 80 to adjust to the user's leg in a natural manner during physical activity. In one embodiment, the strap tab cap 20 is provided with the ability to rotate 15° in either direction from the neutral position. However, in yet another advantageous feature, the washer 40 may be constructed to provide a wide variety of rotational limits, such as, for example, 5°, 10°, 20°, 30°, 45° or 60° in either direction. Furthermore, those of skill in the art will appreciate that the washer may be provided without flanges, or no washer may be provided at all, such that the cap may be rotatable 360° relative to the frame.

Figure 7:
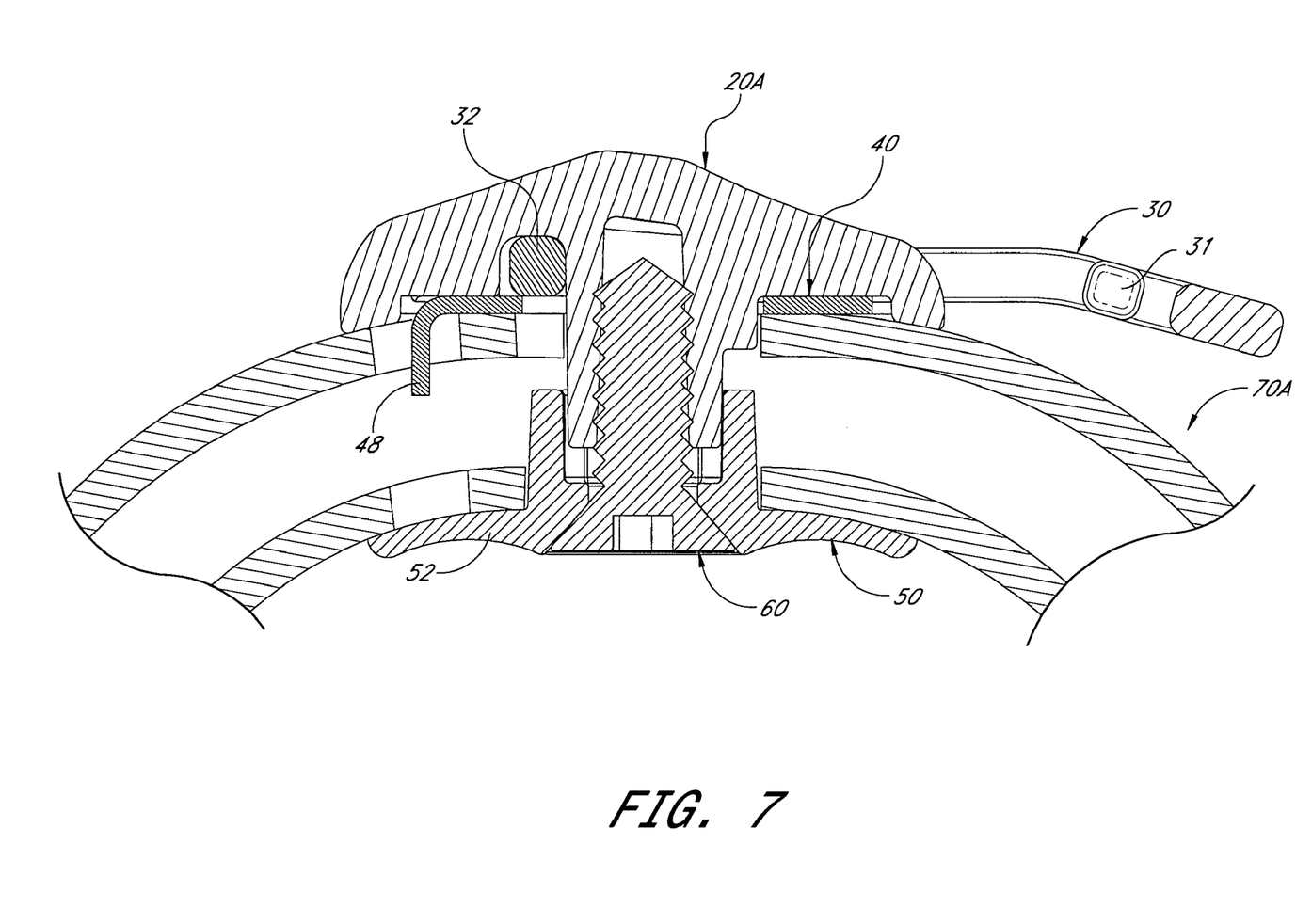
FIG. 7 is a cross-sectional view of the strap tab cap assembly mounted on a curved knee brace frame.

With reference now to FIG. 7, the strap tab cap assembly 10 is shown in combination with a curved knee brace frame 70A. As illustrated in this view, the components of the strap tab cap assembly may be used with knee brace frames having a wide variety of shapes. Due to the curved shape of the frame 70A, the retaining washer 40 may not lay flat along the outer surface of the frame. However, despite this, the downwardly extending tab 48 on the washer 40 is configured with sufficient length to extend into the hole 74 in the frame 70A for preventing the washer 40 from rotating relative to the frame. Furthermore, in the illustrated embodiment, the body 52 of the bushing 50 is fabricated from a flexible material for conforming to the inner surface of the frame 70A. The strap tab cap 20A is shaped to conform to the outer surface of the frame 70A. As discussed above, the strap tab cap 20A and bushing 50 are slidably coupled for adjusting to the particular frame thickness.

From the foregoing, it will be appreciated that each of the preferred embodiments of the strap tab cap assembly can be attached to a knee brace frame quickly and easily and has excellent structural integrity. In addition, the each of the preferred embodiments of the strap tab cap assembly is very versatile and can be used in a broad range of other applications, such as, for example, on luggage or backpacks, wherein a strap may be used. Furthermore, those of skill in the art will appreciate that the present strap tab cap assembly could embody alternate configurations from those disclosed above. For example, the strap tab cap could be insert molded. In one advantageous feature, such a strap tab cap might provide a lower profile and/or increased strength. In addition, the fastening member need not be inserted from the inside of the frame. Rather, in one alternative embodiment, it may be inserted through a hole on the top of the cap and threaded into a blind or through a hole in the bushing.

In summary, the above description presents the best mode contemplated for a rotatable strap tab cap according to the present invention, and of the manner and process of making and using it, in such full, clear, concise, and exact terms as to enable any person skilled in the art to which it pertains to make and use this invention. However, the embodiments of the strap tab cap described herein are susceptible to modifications and alternate constructions that are fully equivalent. Consequently, it is not the intention to limit this strap tab cap to the particular embodiments disclosed. On the contrary, the intention is to cover all modifications and alternate constructions coming within the spirit and scope of the invention as generally expressed by the following claims, which particularly point out and distinctly claim the subject matter of the present invention.

What is claimed is:

1. A strap tab cap assembly for attaching a strap tab to a knee brace frame, comprising:
    a strap tab cap having a main body with a bottom side, the strap tab cap being formed with a cap shaft extending from the bottom side, the cap shaft being formed to extend into a first hole in the knee brace frame;
    a channel extending along the bottom side of the main body, the channel sized to receive a first portion of the strap tab for securely attaching the strap tab to the knee brace frame;
    a washer having top and bottom sides and a central hole sized for receiving the cap shaft, the washer having first and second stops extending from the top side and a tab configured for engagement with the knee brace frame for preventing the washer from rotating with respect to the knee brace frame; and
    a fastening member configured for rotatably coupling the strap tab cap to the knee brace frame;
    wherein the washer is provided between an outer surface of the knee brace frame and the bottom side of the main body, the stops being configured to engage a portion of the main body for limiting rotation of the strap tab cap with respect to the knee brace frame.

2. The strap tab cap assembly of claim 1, wherein the cap shaft is formed with a central orifice for receiving a portion of the fastening member.

3. The strap tab cap assembly of claim 2, wherein the fastening member is a threaded screw and the cap shaft is fabricated for receiving the screw.

4. The strap tab cap assembly of claim 1, further comprising a bushing disposed along an inner surface of the knee brace and having a central hole sized for receiving the fastening member.

5. The strap tab cap assembly of claim 4, wherein the bushing further comprises a bushing shaft configured to extend into the first hole in the knee brace frame.

6. The strap tab cap assembly of claim 5, wherein the bushing shaft and the cap shaft are slidably engageable.

7. The strap tab cap assembly of claim 6, wherein the bushing shaft and the cap shaft have complementary cross-sections for maintaining the bushing and the strap tab cap in a rotatably fixed relationship.

8. The strap tab cap assembly of claim 4, wherein the bushing includes a substantially disc-shaped body that is flexible for conforming to a curved shape along the inner surface of the knee brace frame.

9. The strap tab cap assembly of claim 1, wherein the tab protrudes from the bottom side of the washer, the tab being configured to extend into a second hole in the knee brace frame.

10. The strap tab cap assembly of claim 1, wherein the channel is defined at least in part by a wall extending along the bottom side of the main body, the wall being configured to engage at least one of the stops for limiting rotation of the strap tab cap.

11. The strap tab cap assembly of claim 1, wherein the first and second stops are flanges.

12. The strap tab cap assembly of claim 1, wherein the main body has a substantially round shape.

13. The strap tab cap assembly of claim 1, wherein the strap tab includes a second portion for receiving a strap, the second portion located on the opposite side of the fastening member as the first portion such that the first portion is pulled toward the fastening member during use.

14. A strap tab cap assembly for attaching a strap tab to a knee brace frame, comprising:
    a strap tab cap having a main body with a bottom side, the strap tab cap being formed with a cap shaft extending from the bottom side, the cap shaft being formed to extend into a hole in the knee brace frame;
    a channel extending along the bottom side of the main body, the channel sized to receive a first portion of the strap tab for securely attaching the strap tab to the knee brace frame;
    a bushing disposed along an inner surface of the knee brace and having a bushing shaft formed to extend into the hole and sized for slidable engagement with the cap shaft, the bushing shaft and the cap shaft having complementary cross-sections for maintaining the bushing and the strap tab cap in a rotatably fixed relationship.

15. The strap tab cap assembly of claim 14, wherein a distance between the bushing and strap tab cap is adjustable for conforming to the thickness of the knee brace frame.

16. The strap tab cap assembly of claim 15, wherein the washer is rotatably fixed with respect to the knee brace frame.

17. The strap tab cap assembly of claim 14, further comprising a fastening member configured for securing the bushing to the strap tab cap.

18. The strap tab cap assembly of claim 17, wherein the bushing includes a central hole for receiving the fastener along an inner surface of the knee brace frame.

19. The strap tab cap assembly of claim 14, further comprising a washer disposed between an outer surface of the knee brace frame and the bottom side of the main body for protecting the knee brace frame from wear.

20. The strap tab cap assembly of claim 14, wherein the bushing shaft and the cap shaft define a pivotal axis for the strap tab cap so as to allow the strap tab cap to pivot.

21. A strap tab cap assembly for attaching a strap tab to a knee brace frame, comprising:
    a strap tab cap having a main body with a bottom side, the strap tab cap being formed with a cap shaft extending from the bottom side, the cap shaft being formed to extend into a hole in the knee brace frame;
    a channel extending along the bottom side of the main body, the channel sized to receive a first portion of the strap tab for securely attaching the strap tab to the knee brace frame;
    a bushing disposed along an inner surface of the knee brace and having a bushing shaft formed to extend into the hole and sized for slidable engagement with the cap shaft, the bushing shaft and the cap shaft having complementary cross-sections for maintaining the bushing and the strap tab cap in a rotatably fixed relationship, wherein a distance between the bushing and strap tab cap is adjustable for conforming to the thickness of the knee brace frame, wherein the washer is rotatably fixed with respect to the knee brace frame, and wherein the washer has at least one stop configured to engage a portion of the main body for limiting rotation of the strap tab cap.

22. A strap tab retainer for connection to an article having a wall with a hole extending therethrough, comprising:
   a first strap tab;
   a washer having a central hole intended for alignment with a hole in the article wall, the washer having a structure matable with the article wall to prevent rotation of the washer;
   a clamp engaging an interior surface of the wall of the article and an exterior surface of the washer, the clamp rotatable in the hole and holding a portion of the first strap tab against the top surface of the washer, the washer having stops engageable with the rotatable clamp;
   whereby limited rotation of the strap tab is permitted by rotation of the clamp while the washer remains substantially stationary with respect to the article.

23. The strap tab retainer of claim 22, wherein the clamp includes a first channel sized for receiving the portion of the first strap tab.

24. The strap tab retainer of claim 23, wherein the clamp further includes a second channel sized for receiving a portion of a second strap tab.

25. The strap tab retainer of claim 23, wherein the first channel is defined at least in part by a wall extending along the clamp, the wall being configured to engage at least one of the stops for limiting rotation of the clamp.

26. The strap tab retainer of claim 22, wherein the washer is formed with a downwardly extending protrusion for engaging the wall of the article.

27. The strap tab retainer of claim 22, wherein the washer includes two upwardly extending protrusions for providing the stops.

28. A method, comprising:
   providing a knee brace having an outer surface;
   disposing a washer along the outer surface of the knee brace frame, the washer having a bottom side engaging the knee brace frame and a top side facing away from the knee brace frame;
   securing a portion of a strap tab for rotatable movement over the top side of the washer, the strap tab configured to hold a securing strap for assisting in securing the knee brace to a user's leg;
   rotating the strap tab with respect to the outer surface of the washer while maintaining the washer substantially stationary with respect to the knee brace; and
   limiting the rotation of the strap tab to a limited range of rotation with the washer.

* * * * *